US00PP07895P

United States Patent [19]

Marciel

[11] Patent Number: Plant 7,895

[45] Date of Patent: Jun. 30, 1992

[54] TEA ROSE NAMED DEVNINA

[75] Inventor: Stanley G. Marciel, Aptos, Calif.

[73] Assignee: DeVor Nurseries, Inc., Watsonville, Calif.

[21] Appl. No.: 615,155

[22] Filed: Nov. 19, 1990

[51] Int. Cl.[5] ..... A01H 5/00
[52] U.S. Cl. ..... Plt./18
[58] Field of Search ..... Plt./18

*Primary Examiner*—James R. Feyrer
*Attorney, Agent, or Firm*—Charles W. Rummler

[57] ABSTRACT

A new and distinct tea rose particularly distinguished by its continuous and profuse production of large flowers having an Orchid Pink to Orient Pink coloration, carried singly on long, strong upright stems of a plant having a vigorous and upright growth habit and an abundant production of foliage of relatively large size.

1 Drawing Sheet

BACKGROUND OF THE NEW PLANT

This new tea rose originated as a seedling hybrid produced by me at my nursery at Pleasanton, Calif. by crossing an unnamed seedling, selected from my collection of tea rose plants maintained at Pleasanton for breeding purposes, with pollen from the variety 'Pink Puff' (U.S. Plant Pat. No. 2,634) and the present seedling of that hybridization was selected by me for propagation because of the unusual Light to Medium Pink coloration of its large blossoms and the vigorous upright growth habit on a plant having strong upright stems and abundant foliage of relatively large size. Propagation of this selected seedling was done by me at Pleasanton, by budding with such success that under my direction, propagation of this new plant was continued through several successive generations to establish that the novel characteristics of the selected seedling would hold true from generation to generation and appeared to be so fixed that the homogeneity of this plant could be assured.

DESCRIPTION OF THE DRAWING

This new tea rose plant is illustrated by the accompanying full color photographic drawing which shows views of several of its flowers at different stages of progress to maturity, the color rendition being as nearly true to that as herein specified as is possible to obtain by conventional photographic procedures.

DESCRIPTION OF THE NEW VARIETY

The followng is a detailed description of my new tea rose based upon observation of plants grown in greenhouse at Pleasanton, Calif. with the color designations being according to The R.H.S. Color Chart published by The Royal Horticultural Society of London, England.

THE PLANT

Origin: Seedling.
Parentage:
*Seed parent.*—An unnamed seedling selected from my collection of tea roses maintained at Pleasanton for breeding purposes.
*Pollen parent.*—The variety 'Pink Puff' U.S. Plant Pat. No. 2,634.
Classification:
*Botanic.*—Hybrid tea rose.

*Commercial.*—Greenhouse rose.
Form: Upright bush of medium height.
Growth habit: Vigorous, strong and upright.
Main stem:
*Length.*—About 38 to 40 cm. from last flower cut.
Branching character: Free branching.
Foliage:
*Quantity.*—Abundant.
*Number of leaves.*—6 from last flower cut.
*Size.*—About 112 mm. long and about 70 mm. wide.
*Shape.*—Ovate.
*Leaflets.*—Number: 3 or 5. Size: About 61 mm. long and 40 mm. wide. Shape: Generally elliptic with denticulate margins. Texture: Leathery. Aspect: Smooth and glossy. Color: Upper side — Green 137-A. Under side — Yellow Green 147-B. Stipules: Hairy adnate. Rachis: About 25 mm. long on 3 part leaf and about 53 mm. long on 5 part leaf. Petioles: About 14 to 17 mm. long.
Ribs and veins: Depressed on upper side and rounded on lower side.

THE BUD

Size: Medium commercial.
*Diameter.*—About 18 mm.
*Length.*—About 33 mm.
Shape: Slender and tapering.
Rate of opening: Slow.
Color of petals:
*When sepals first divide.*—Red 50-D.
*When petals begin to unfurl.*—Neyron Rose 56-A.
Sepals:
*Number.*—5.
*Shape.*—Spreading with small leafs protruding.
*Character.*—Hooded over the bud and curling back when flowers open.
*Color.*—Inside — Yellow Green 147-D with Yellow Green 147-C nearing the tip. Outside — Yellow Green 144-A.
Calyx:
*Shape.*—Funnel-shaped.
*Size.*—Medium, about 10 mm. wide and 9 mm. long.
*Splitting.*—The calyx does not split.
*Aspect.*—Smooth.
Flower stem:
*Length.*—About 85 to 100 mm.

*Character.*—Slender and erect.
*Color.*—Yellow Green 144-B.

THE FLOWER

Blooming habit: Continuous and profusely, blooming freely under greenhouse conditions.
Size of bloom: Large.
*Diameter.*—About 70 mm. by 67 mm.
*Depth.*—About 36 mm.
Borne: Singly on strong upright stems.
Form:
*When bloom first opens.*—High center.
*When bloom matures.*—Nicely imbricated.
Petalage:
*Number.*—22.
*Number of florets.*—4 or 5.
*Arrangement.*—Imbricated.
*Form.*—Spoon shaped with slightly lobed apex.
*Texture.*—Soft.
*Aspect.*—Velvety.
*Color.*—Outer petals body — Orchid Pink 62-D with base of Chartruese Green 1-C. Reverse side — Red 56-A with base of Chartruese Green 1-D. Inside Petals body — Orient Pink 36-C with base of Yellow 3-D. Reverse side — Red 50-D with base of Yellow 2-D.
*Petaloids.*—Number: 4 or 5. Size: About 15 mm. Color: Red 39-D with base of Chrome Yellow 1-C.
Peduncle:
*Length.*—About 85 to 100 mm.
*Color.*—Yellow Green 144-B.
*Character.*—Sturdy and upright.
Persistence: The flowers hang on and dry.

Disease resistance: Resistant to mildew, rust and black spots as observed at Pleasanton, Calif.
Fragrance: Slight.
Lasting quality: Long lasting on plant and as a cut flower.

THE REPRODUCTIVE ORGANS

Stamens:
*Number.*—About 120 to 128.
*Arrangement.*—Introrse.
*Anthers.*—Size: About 2½ mm. Color: Greyed Orange 167-C.
*Filaments.*—Length: About 8 mm. Color: Yellow Green 154-D.
*Pollen.*—Color: Greyed Orange 167-C.
Pistils:
*Number.*—About 86 to 92.
*Styles.*—Length: 7 mm. Color: Yellow 2-D.
*Stigmas.*—Color: Yellow 11-C.
Character of the ovaries: Slender, oblong, slightly flattened and covered with silvery hairs.

THE FRUIT

Fertility: The fruit is fertile.
Shape: Pear shaped.
Color at maturity: Greyed Orange 163-B.

I claim:

1. The new and distinct variety of tea rose substantially as herein shown and described, particularly characterized by its profuse and continuous free blooming habit under greenhouse conditions, the flowers being of large size and having an Orchid Pink to Orient Pink coloration; the plant being further distinguished by its vigorous free branching growth habit and its abundant foliage.

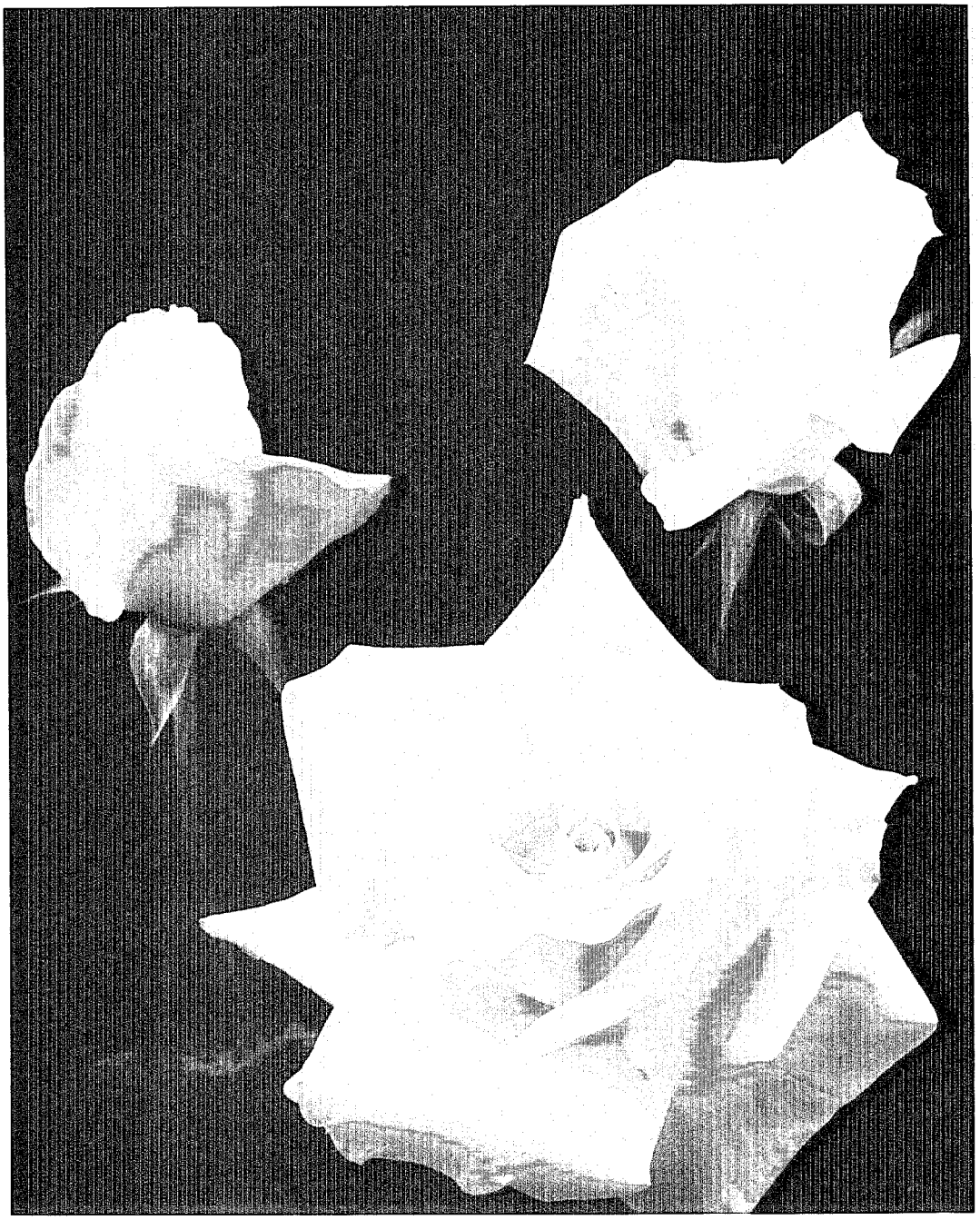

* * * * *